United States Patent [19]

Steele et al.

[11] Patent Number: 5,081,047

[45] Date of Patent: Jan. 14, 1992

[54] ZERO GRAVITY COMPATIBLE TOTAL CARBON AND ORGANIC CARBON ANALYZER

[75] Inventors: John W. Steele, Torrington; Philip J. Birbara, Windsor Locks; Timothy A. Nalette, Tolland, all of Conn.

[73] Assignee: United Technologies Corporation, Hartford, Conn.

[21] Appl. No.: 544,768

[22] Filed: Jun. 27, 1990

[51] Int. Cl.[5] .............................................. G01N 33/00
[52] U.S. Cl. ..................... 436/146; 436/125; 436/178; 436/139; 436/160; 436/161; 422/89; 422/93; 73/23.41
[58] Field of Search ................ 422/89, 93; 436/177, 436/178, 139, 140, 141, 158, 160, 161, 162, 145, 146, 125; 73/23.41

[56] References Cited

U.S. PATENT DOCUMENTS

| | | | |
|---|---|---|---|
| 3,672,841 | 6/1972 | Freeman et al. | 23/230 PC |
| 3,958,941 | 5/1976 | Regan | 23/253 PC |
| 4,273,558 | 6/1981 | Mar | 23/230 PC |
| 4,288,229 | 9/1981 | Mar | 422/79 |
| 4,628,726 | 12/1986 | Heikkila et al. | 73/61.1 C |
| 4,694,682 | 9/1987 | Heikkila et al. | 73/61.1 C |
| 4,775,476 | 10/1988 | Melcher et al. | 210/635 |

*Primary Examiner*—David L. Lacey
*Assistant Examiner*—Abanti B. Singla
*Attorney, Agent, or Firm*—Alan C. Cohen; Pamela J. Mercier

[57] ABSTRACT

Total carbon and organic carbon monitoring of water is useful in determining water quality. Conventional TOC monitoring techniques are not zero gravity compatible. Ion chromatography allows for a single phase zero gravity compatible TOC monitoring technique. The ion chromatograph determines the amounts of organic acids and carbonate present in an aqueous sample before and after oxidation. The quantities determined by this technique can be related to the total carbon and the total organic carbon present in the aqueous sample.

10 Claims, 1 Drawing Sheet

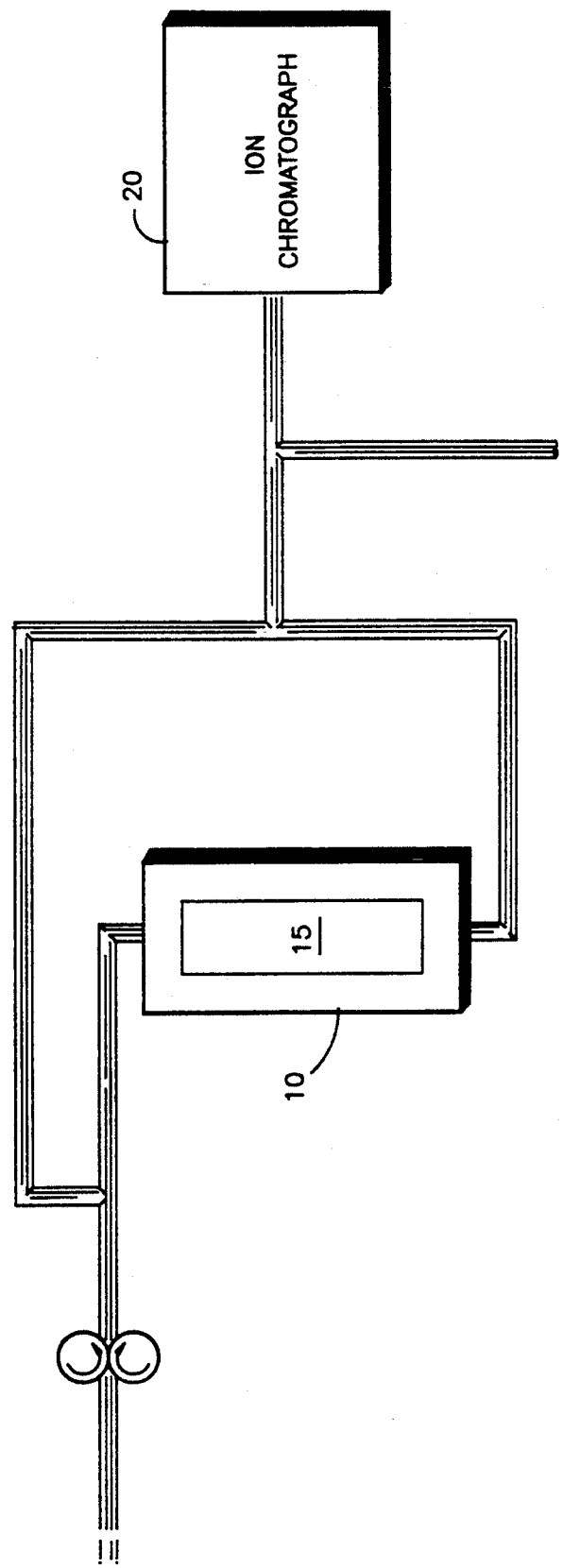

ZERO GRAVITY COMPATIBLE TOTAL CARBON AND ORGANIC CARBON ANALYZER

CROSS REFERENCE

This application relates to copending, U.S. patent application Ser. No. 07/544,766, for TOTAL ORGANIC HALOGEN ANALYZER, filed on June 27, 1990; U.S. patent application Ser. No. 07/544,764, for AUTOMATED BIOLUMINESCENCE MICROBIAL MONITOR, filed June 27, 1990; U.S. patent application Ser. No. 07/544,767, for ZERO GRAVITY COMPATIBLE TOTAL ORGANIC AND INORGANIC CARBON ANALYZER, filed June 27, 1990; U.S. patent application Ser. No. 07/544,765, for AN ELUANT AND PREPARATION APPARATUS AND METHOD FOR USING THE SAME, filed June 27, 1990; and U.S. patent application Ser. No. 07/544,763, for ZERO GRAVITY PURGE AND TRAP FOR MONITORING VOLATILE ORGANIC COMPOUNDS, filed June 27, 1990, all commonly assigned.

1. Technical Field

This invention relates to a carbon analyzer, and especially to a zero gravity compatible total carbon and organic carbon analyzer capable of detecting carbon present in an aqueous solution.

2. Background Art

Water quality monitoring is necessary in many fields for numerous applications, especially if the water is to be used in applications requiring ultra pure water.

One conventional means for assessing water quality is a total organic carbon (TOC) analysis. This analytical procedure requires adjusting the water sample pH to below 3 in order to convert major sources of inorganic carbon, carbonate and bicarbonate ions, to carbon dioxide. The carbon dioxide is purged from the sample with an inert gas, dried, and sent to a calibrated non-dispersive infrared analyzer (NDIR) for carbon dioxide analysis. The total inorganic carbon (TIC) in the water sample is related to the carbon dioxide content which is measured by the NDIR.

Once the inorganic carbon has been removed from the sample, the organic carbon is oxidized in the presence of an oxidant and ultraviolet (UV) radiation, again forming carbon dioxide. The carbon dioxide, as with the TIC carbon dioxide, is purged, dried, and measured by the NDIR analyzer.

This process, although effective, is not zero gravity compatible due to the two phase mixture. Therefore, what is needed in the art is a zero gravity compatible total carbon and organic carbon analysis process and apparatus.

DISCLOSURE OF INVENTION

The present invention is a method and apparatus for total carbon and organic carbon analysis which uses an ion chromatograph and is zero gravity compatible. The ion chromatograph approach uses an oxidation chamber, a means for oxidizing organic carbon in an aqueous sample, and an ion chromatograph. An aqueous sample is initially tested in the ion chromatograph for background carbonate, and then oxidized in the oxidation chamber to produce organic acids and carbonate. The oxidized aqueous sample is then tested in the ion chromatograph for organic acids and carbonate. The total carbon present in the aqueous sample is equal to the amount of organic acids and carbonate present post-oxidation, while the total organic carbon present in the aqueous sample is equivalent to the amount of organic acids and carbonate present in the aqueous sample post-oxidation minus the amount of background carbonate.

The foregoing and other features and advantages of the present invention will become more apparent from the following description and accompanying drawing.

BRIEF DESCRIPTION OF DRAWINGS

The FIGURE is a schematic of a possible embodiment of the ion chromatography approach to total organic carbon analysis.

BEST MODE FOR CARRYING OUT THE INVENTION

This invention discloses an approach and apparatus for total carbon and total organic carbon monitoring of aqueous which is zero gravity compatible. Referring to the FIGURE, which is meant to be exemplary not limiting, the apparatus is comprised of an oxidation chamber (10) with a means for producing ultraviolet (UV) radiation (15), and an ion chromatograph (20).

The process comprises testing for background carbonate by passing part of the aqueous sample directly through the ion chromatograph (20), bypassing the oxidation chamber (10). Ion chromatography, conventionally known in the art for testing organic acids and carbonate, is a process of passing an ionic species through a column and then a detector. Within the column, the ionic species undergoes an adsorption/desorption process. Retention times among ionic species vary. Therefore, certain ionic species reach the detector before others. As a result, it is possible to identify amounts and types of ionic species present.

Upon completion of the background analysis, the remainder of the aqueous sample is passed through the oxidation chamber (10) to convert the organic compounds in the aqueous sample to carbonate and low molecular weight organic acids. Typically, if the concentration of organic compounds in the aqueous sample is low, less than about 5 ppm (parts per million), there is sufficient oxygen dissolved in the aqueous sample for the oxidation. Therefore, the organic compounds are oxidized using dissolved oxygen in combination with UV radiation. Note, if the aqueous sample is oxygen free, a source of oxygen will be necessary for the oxidation. The means for producing UV radiation (15) can be any means conventionally known in the art. Typically, UV radiation is produced with a lamp or bulb. The lamp or bulb can be any frequency in the UV region of the spectrum, with a mercury vapor lamp or bulb preferred. If the organic compound concentration in the aqueous sample is greater than about 5 ppm, the organic compounds can be oxidized with an oxidant or a combination of an oxidant and UV radiation. The oxidant can be any source of oxygen which does not adversely affect the monitoring process, such as sodium dichromate and potassium persulfate. Whether UV radiation, an oxidant, or a combination thereof should be utilized can easily be determined by an artisan.

The organic acids and carbonate are then analyzed in the ion chromatograph (20) as described above. The difference between the amount of the post-oxidation carbonate and organic acid and the pre-oxidation carbonate concentration is related to the total organic carbon content in the aqueous sample.

The ion chromatography apparatus is zero gravity compatible, an improvement over the prior art. Additionally, the apparatus is capable of complete automation.

Although this invention has been shown and described with respect to detailed embodiments thereof, it will be understood by those skilled in the art that various changes in form and detail thereof may be made without departing from the spirit and scope of the claimed invention.

We claim:

1. An apparatus for total organic carbon analysis of an aqueous solution which is zero gravity compatible, which comprises:
   a. an oxidation chamber;
   b. a means for introducing an aqueous sample to a first portion of said oxidation chamber;
   c. a means for oxidizing organic carbon present in said first portion of said aqueous sample in said oxidation chamber, said means for introducing aqueous sample in flow communication with said means for oxidizing;
   d. a means for by-passing a second portion of said aqueous sample from the oxidation chamber;
   e. an ion chromatograph for analyzing the aqueous sample said ion chromatograph also in flow communication with said means for bypassing; and
   e. said ion chromatograph in flow communication with said means for bypassing a means for introducing said first portion of said aqueous sample to said ion chromatograph.

2. An apparatus as in claim 1 wherein the means for oxidizing the organic carbon is selected from the group consisting of an oxidant, ultraviolet lamps and bulbs having frequencies in the ultraviolet region of the spectrum, and combinations thereof.

3. A method for analyzing for the total organic carbon concentration in an aqueous solution which is zero gravity compatible, which comprises:
   a. using an ion chromatograph to test for background carbonate present in said aqueous sample;
   b. oxidizing any organic compounds in the aqueous sample to produce organic acids and carbonate;
   c. using said ion chromatograph to test for said organic acids and carbonate in the oxidized aqueous sample;
   (d) employing the analyzed organic acids and carbonate present in the aqueous sample to provide the total organic carbon present in the aqueous sample.

4. A method as in claim 3 wherein the organic compounds are oxidized using ultraviolet radiation.

5. A method as in claim 3 wherein the organic compounds are oxidized using a combination of ultraviolet radiation and an oxidant.

6. A zero gravity compatible apparatus for total carbon analysis of an aqueous solution, which comprises:
   a. an oxidation chamber for oxidizing any organic carbon in an aqueous sample;
   b. a means for oxidizing the organic carbon in the aqueous sample;
   c. a means for introducing the aqueous sample to said oxidation chamber wherein said means for oxidizing is in flow communication with said means for introducing;
   d. an ion chromatograph for analyzing said oxidized aqueous sample; and
   e. a means for introducing the aqueous sample to said ion chromatograph wherein said ion chromatograph is in flow communication with said means for introducing the oxidized aqueous sample to said ion chromatograph.

7. An apparatus as in claim 6 wherein the means for oxidizing the organic carbon is selected from the group consisting of an oxidant, ultraviolet lamps and bulbs having frequencies in the ultraviolet region of the spectrum, and combinations thereof.

8. A zero gravity compatible method to determine the concentration of total carbon in an aqueous solution, which comprises:
   a. oxidizing any organic compounds in an aqueous sample to produce organic acids and carbonate;
   b. using an ion chromatograph to analyze the organic acids and carbonate in the oxidized aqueous sample; and
   c. employing the ion chromatograph analysis of the organic acids and carbonate present in the aqueous sample to determine the total carbon present in the aqueous sample.

9. A method as in claim 8 wherein the organic compounds are oxidized using ultraviolet radiation.

10. A method as in claim 8 wherein the organic compounds are oxidized using a combination of ultraviolet radiation and an oxidant.

* * * * *